(12) United States Patent
Craig et al.

(10) Patent No.: US 9,962,245 B2
(45) Date of Patent: May 8, 2018

(54) DENTAL COMPOSITIONS, MILL BLOCKS, AND METHODS

(75) Inventors: Bradley D. Craig, Lake Elmo, MN (US); Ryan E. Johnson, Peoria, IL (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days. days.

(21) Appl. No.: 13/516,981

(22) PCT Filed: Dec. 22, 2010

(86) PCT No.: PCT/US2010/061748
§ 371 (c)(1),
(2), (4) Date: Jan. 16, 2014

(87) PCT Pub. No.: WO2011/087832
PCT Pub. Date: Jul. 21, 2011

(65) Prior Publication Data
US 2014/0162216 A1    Jun. 12, 2014

Related U.S. Application Data

(60) Provisional application No. 61/289,041, filed on Dec. 22, 2009.

(51) Int. Cl.
| | |
|---|---|
| *A61C 8/00* | (2006.01) |
| *A61L 24/02* | (2006.01) |
| *C08K 3/34* | (2006.01) |
| *A61C 13/00* | (2006.01) |
| *C08K 9/02* | (2006.01) |

(52) U.S. Cl.
CPC .......... *A61C 13/0022* (2013.01); *A61C 8/005* (2013.01); *C08K 9/02* (2013.01); *A61L 2430/12* (2013.01)

(58) Field of Classification Search
USPC ...................................... 433/201.1; 523/115
See application file for complete search history.

(56) References Cited

U.S. PATENT DOCUMENTS

| | | | |
|---|---|---|---|
| 4,298,738 A | 11/1981 | Lechtken | |
| 4,324,744 A | 4/1982 | Lechtken | |
| 4,356,296 A | 10/1982 | Griffith | |
| 4,362,842 A | 12/1982 | Masuhara | |
| 4,385,109 A | 5/1983 | Lechtken | |
| 4,503,169 A | 3/1985 | Randklev | |
| 4,642,126 A | 2/1987 | Zador | |
| 4,648,843 A | 3/1987 | Mitra | |
| 4,652,274 A | 3/1987 | Boettcher | |
| 4,665,217 A | 5/1987 | Reiners | |
| 4,695,251 A | 9/1987 | Randklev | |
| 4,707,504 A | 11/1987 | Walkowiak | |
| 4,710,523 A | 12/1987 | Lechtken | |
| 4,737,593 A | 4/1988 | Ellrich | |
| 4,752,338 A | 6/1988 | Reiners | |
| 5,026,902 A | 6/1991 | Fock | |
| 5,076,844 A | 12/1991 | Fock | |
| 5,545,676 A | 8/1996 | Palazzotto | |
| 5,990,195 A | 11/1999 | Arita | |
| 6,030,606 A | 2/2000 | Holmes | |
| 6,251,963 B1 | 6/2001 | Köhler | |
| 6,283,753 B1 | 9/2001 | Willoughby | |
| 6,365,771 B1 | 4/2002 | Suzuki | |
| 6,376,590 B2 | 4/2002 | Kolb | |
| 6,387,981 B1 | 5/2002 | Zhang | |
| 6,572,693 B1 | 6/2003 | Wu | |
| 6,730,156 B1 | 5/2004 | Windisch | |
| 6,765,036 B2 | 7/2004 | Dede | |
| 6,787,584 B2 | 9/2004 | Jia | |
| 6,818,682 B2 | 11/2004 | Falsafi | |
| 6,899,948 B2 | 5/2005 | Zhang | |
| 7,255,562 B2 | 8/2007 | Rusin | |
| 7,335,250 B2 * | 2/2008 | Burtscher et al. ............... | 106/35 |
| 7,429,422 B2 | 9/2008 | Davidson | |
| 8,722,759 B2 * | 5/2014 | Craig ..................... | A61K 6/083 433/222.1 |
| 2002/0022677 A1 | 2/2002 | Teramae | |
| 2003/0031984 A1 | 2/2003 | Rusin | |

(Continued)

FOREIGN PATENT DOCUMENTS

| | | |
|---|---|---|
| CN | 101595139 | 12/2009 |
| EP | 0173567 A2 | 3/1986 |
| GB | 2291053 B | 3/1997 |
| WO | WO 2000-038619 | 7/2000 |
| WO | WO 2000-042092 | 7/2000 |
| WO | WO 2001-007444 | 2/2001 |
| WO | WO 2001-092271 | 12/2001 |
| WO | WO 2003-063804 | 8/2003 |
| WO | WO 2005/117805 | 12/2005 |
| WO | WO 2006/055329 | 5/2006 |
| WO | WO 2008/033911 | 3/2008 |
| WO | WO 2010-029515 | 3/2010 |
| WO | WO 2010-088754 | 8/2010 |

OTHER PUBLICATIONS

Supplementary European Search Report for EP 10 84 3569 dated Oct. 22, 2014.
Adamson, "Aminoalkyl Tertiary Carbinols and Derived Products. Part I. 3-Amino-1 : 1-diphenylpropan-1-ols," JCSOA9; J. Chem. Soc.; (1949); spl. 144,152.
International Search Report for PCT/US10/61748, dated Feb. 24, 2011, 5 pages.

*Primary Examiner* — Tae H Yoon (57) ABSTRACT

A dental composition comprising a polymerizable resin comprising ethylenically unsaturated groups; a thermally activated initiator dissolved in the resin; and an inorganic filler combined with the resin in an amount greater than about 60 percent by weight based upon the weight of the composition; wherein the initiator is activated at a temperature of about 100 to about 150° C. to provide free radicals; and wherein the filler has a surface area of at least about 65 square meters per gram filler; a dental mill block comprising the thermally cured composition, a method of manufacturing the dental mill block, and a kit comprising a plurality of the mill blocks are provided.

17 Claims, 1 Drawing Sheet

(56) References Cited

U.S. PATENT DOCUMENTS

| | | |
|---|---|---|
| 2005/0252413 A1 | 11/2005 | Kangas |
| 2005/0252414 A1 | 11/2005 | Craig |
| 2005/0252415 A1* | 11/2005 | Budd ............... A61K 6/0017 106/35 |
| 2005/0256223 A1 | 11/2005 | Kolb |
| 2008/0085494 A1 | 4/2008 | Mader |
| 2008/0153054 A1 | 6/2008 | Masters |
| 2008/0160206 A1 | 7/2008 | Burtscher |
| 2010/0048762 A1 | 2/2010 | Ishino |
| 2011/0171609 A1* | 7/2011 | Yang ............... A61K 6/0008 433/228.1 |
| 2011/0229858 A1 | 9/2011 | Sadoun |

* cited by examiner

DENTAL COMPOSITIONS, MILL BLOCKS, AND METHODS

CROSS REFERENCE TO RELATED APPLICATIONS

This application is a national stage filing under 35 U.S.C. 371 of PCT/US2010/061748, filed Dec. 22, 2010, which claims priority to U.S. Provisional Application No. 61/289,041, filed Dec. 22, 2009, the disclosure of which is incorporated by reference in its/their entirety herein.

BACKGROUND

Fabricating custom-fit dental prosthetics, such as restoratives, tooth replacements, inlays, onlays, veneers, full and partial crowns, bridges, implants, posts, and the like has been practiced for some time. Materials used to make the prostheses include, for example, gold, ceramics, amalgam, porcelain, and composites. A conventional process for making certain dental prosthetics involves taking an impression of a dentition using an elastomeric material from which a cast model is made to replicate the dentition. The prosthetic is then produced from the model using metal, ceramic or a composite material, followed by making modifications for proper fit and comfort. More recently, working time has been greatly reduced using digital dentistry wherein computer automation is combined with optics, digitizing equipment, CAD/CAM and milling tools. Fabrication of a dental prosthetic or other types of prostheses using these methods requires a mill blank, a solid block of material from which the prosthetic is cut or carved. Ceramic materials have typically been used as the mill block. Certain composite materials comprising a polymeric resin and a filler have also been used for this purpose, for example, MZ100 mill blocks available from 3M ESPE.

SUMMARY

It has now been found that a composite mill block with significantly improved strength, wear, and aesthetic properties can be made using the composition provided herein. In addition, the composite mill blocks can be produced through a more manufacturing-friendly process.

Accordingly, in one embodiment, there is provided a dental composition comprising:
a polymerizable resin comprising an ethylenically unsaturated group;
a thermally activated initiator dissolved in the resin; and
an inorganic filler combined with the resin in an amount greater than 60 percent by weight based upon the weight of the composition;
wherein the initiator is activated at a temperature of about 100 to about 150° C. to provide free radicals; and
wherein the filler has a surface area of at least 65 square meters per gram filler.

In another embodiment, there is provided a dental mill block comprising a thermally cured composition comprising:
a polymerized resin which is a free-radial initiated addition polymerization product of a polymerizable resin comprising methacryloyl groups; and
an inorganic filler dispersed in the polymerized resin;
wherein the inorganic filler has a surface area of at least 65 square meters per gram filler and is present in the polymerized resin in amount greater than 60 percent by weight based upon the weight of the composition; and
wherein the composition is thermally cured by thermally activating an initiator dissolved in the polymerizable resin, the initiator being activated at a temperature of about 100 to about 150° C. In some embodiments, the polymerizable resin comprising an ethylenically unsaturated group comprises a methacryloyl group.

In another embodiment, there is provided a method of manufacturing a dental mill block, the method comprising:
providing a composition comprising:
a polymerizable resin comprising methacryloyl groups;
a thermally activated initiator dissolved in the resin; and
an inorganic filler combined with the resin in an amount greater than 60 percent by weight based upon the weight of the composition;
wherein the initiator is activated at a temperature of about 100 to about 150° C. to provide free radicals; and
wherein the filler has a surface area of at least 65 square meters per gram filler;
shaping the composition into a desired mill block configuration; and
thermally curing the composition at a temperature of about 100 to about 150° C.

In another embodiment, there is provided a kit comprising a plurality of the mill blocks according to any one of the embodiments thereof described herein.

DEFINITIONS

The phrases "blank," "mill blank," "dental mill blank," "dental mill block", "mill block," and "block" can be used interchangeably and generally refer to a solid block of material from which a desired product (e.g., a dental restoration) can be machined, and is not limited to the type of machining that will be used, even if referred to as a "mill" block.

By "nanofiller" is meant a filler having an average primary particle size of at most 200 nanometers. The nanofiller component may be a single nanofiller or a combination of nanofillers. For certain embodiments, the nanofiller comprises non-pyrogenic nanoparticles or nanoclusters.

By "nano structured" is meant a material in a form having at least one dimension that is, on average, at most 200 nanometers (e.g., nanosized particles). Thus, nanostructured materials refer to materials including, for example, nanoparticles as defined herein below; aggregates of nanoparticles; materials coated on particles, wherein the coatings have an average thickness of at most 200 nanometers; materials coated on aggregates of particles, wherein the coatings have an average thickness of at most 200 nanometers; materials infiltrated in porous structures having an average pore size of at most 200 nanometers; and combinations thereof. Porous structures include, for example, porous particles, porous aggregates of particles, porous coatings, and combinations thereof.

As used herein "nanoparticles" "nanosized particles," refer to particles having an average size of at most 200 nanometers. As used herein for a spherical particle, "size" refers to the diameter of the particle. As used herein for a non-spherical particle, "size" refers to the longest dimension of the particle. In certain embodiments, the nanoparticles are comprises of discrete, non-aggregated and non-agglomerate particles.

By "nanocluster" is meant an association of nanoparticles drawn together by relatively weak intermolecular forces that cause them to clump together, i.e. to aggregate. Typically, nanoclusters have an average size of at most 10 micrometers.

The term "comprising" and variations thereof (e.g., comprises, includes, etc.) do not have a limiting meaning where these terms appear in the description and claims.

As used herein, "a," "an," "the," "at least one," and "one or more" are used interchangeably, unless the context clearly dictates otherwise.

Also herein, the recitations of numerical ranges by endpoints include all numbers subsumed within that range (e.g., about 100 to about 150° C. includes 100, 110, 111, 123.1, 137, 140, 145, 149.3, and 150).

The above summary of the present invention is not intended to describe each disclosed embodiment or every implementation of the present invention. The description that follows more particularly exemplifies illustrative embodiments.

DETAILED DESCRIPTION OF ILLUSTRATIVE EMBODIMENTS OF THE INVENTION

As indicated above, the presently provided compositions when thermally cured result in a composite mill block with significantly improved strength, wear, and aesthetic properties. The compositions combine certain thermally activated initiators with certain fillers in a free-radically polymerizable resin as described herein. The initiators are activated at a sufficiently high temperature that premature curing does not take place during normal handling procedures. At the same time, thermal initiation can take place at a sufficiently low temperature to avoid degradation of the other components, such as monomers, causing discoloration and loss of physical properties in the ultimately cured mill block.

The compositions include a high surface area inorganic filler, which in these compositions, after the thermally initiated curing, has been found to result in higher gloss, greater polish retention, and higher strength (e.g., approaching or exceeding that of ceramics) as compared with previous composite materials. In some embodiments, the surface area of the inorganic filler is at least 65 square meters per gram filler. For certain embodiments, the surface area of the inorganic filler is at least 80 square meters per gram filler.

Also, a relatively high level of the high surface area inorganic filler is employed in the compositions. For certain embodiments, the filler is present in an amount of at least 60 percent by weight based upon the weight of the composition. The amount of filler loading dictates mechanical strengths, wear resistance, and other characteristics in the mill block material. Wear resistance, in particular, is highly dependent upon the filler loading, especially as you approach the percolation threshold (maximum loading) for a given distribution. The goal is to maximize filler loading while maintaining processability, and minimizing defects such as voids.

The inorganic filler(s) used in the compositions is typically finely divided. The filler(s) can have a unimodal or polymodal (e.g., bimodal) particle size distribution. For certain embodiments, the maximum particle size (the largest dimension of a particle, generally, the diameter or by volumetric average) of the filler(s) is less than 50 micrometers, less than 10 micrometers, or less than 5 micrometers. In some embodiments, number average particle size of the filler(s) is less than 0.5 micrometers or less than 0.2 micrometer Alternatively, for certain embodiments, the average particle size may be larger, and the material may include particles with a maximum particle size around 40 micrometers.

The filler(s) should be nontoxic and suitable for use in the mouth. The filler(s) can be radiopaque or radiolucent. The filler typically is substantially insoluble in water. The filler(s) may be acid-reactive, non-acid-reactive, or a combination thereof.

Examples of suitable inorganic fillers that may be included in the composition are naturally occurring or synthetic materials including, but not limited to: quartz (i.e. silica, $SiO_2$); nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); submicron silica particles such as pyrogenic silicas (e.g., those available under the trade designations AEROSIL, including OX 50, 130, 150 and 200 (Degussa Corp., Akron, Ohio) and CAB-O-SIL M5 (Cabot Corp., Tuscola, Ill.)) and non-pyrogenic nanoparticles of silica; nanoparticles of zirconia; and zirconia-silica fillers, including those in which the silica and zirconia nanoparticles are clumped together in the form of silica-zirconia nanoclusters. Mixtures of fillers can be used if desired.

The non-pyrogenic nanoparticles of silica and nanoparticles of zirconia may be prepared from dispersions, sols, or solutions of at least one precursor. Process of this nature are describe, for example, in U.S. Pat. No. 4,503,169 (Randklev) and GB Patent No. 2291053 B.

Zirconia-silica filler may be prepared from a silica sol and zirconyl acetate as described, for example, in U.S. Pat. No. 6,818,682 at column 11, line 40 through column 12, line 10. In another example, silica-zirconia nanocluster fillers may be prepared by mixing a nanosilica sol together with a preformed nanozirconia particulate sol. The nanozirconia sol is typically composed of crystalline zirconia nanoparticles. The use of a preformed nanozirconia sol, in certain circumstances, provides for silica-zirconia nanofillers with better opalescence properties than those derived from zirconyl acetate.

The silica sol typically comprises silica particles having a mean diameter from about 10 nm to about 100 nm, more typically from about 15 nm to about 60 nm, most typically from about 15 nm to about 35 nm, with a mean particle diameter of about 20 nm being particularly well-suited for fabrication of nanoclusters. The zirconia sol typically comprises zirconia particles that are small enough to not scatter the majority of visible light, but are large enough to refract shorter wavelength blue light to give the opalescent effect. A zirconia sol having a mean particle size from about 3 nm to about 30 nm is suitable for forming the nanoclusters. Typically, the zirconia particles in the sol have a mean particle diameter from about 5 nm to about 15 nm, more typically from about 6 nm to about 12 nm, and most typically from about 7 nm to about 10 nm. When mixed together under acidic conditions where the sol mixture is stable, such as at a pH of below 2, the preformed zirconia nanoparticles form a structure with the silica nanoparticles on gelling and drying that gives the desired opalescence character while maintaining a high level of optical transparency of the final composite material.

NALCO 1042 silica sol (Nalco Chemical Company, Naperville, Ill.) or other commercially available colloidal silica sols may be used. If a base-stabilized sol is used, typically it will first be subjected to ion exchange in order to remove sodium, for example, with an AMBERLITE IR-120 ion exchange resin, or pH adjusted with nitric acid. It is usually desirable to pH adjust the silica to below 1.2, typically about 0.8 to about 1.0, and then add the zirconia to it slowly, to prevent localized gelation and agglomeration. The pH of the resultant mixture is typically about 1.1 to about 1.2. Suitable colloidal silica sols are available from a variety of vendors, including Nalco (Ondeo-Nalco, Grace chemical), H.C. Stark, Nissan Chemical (Snowtex), Nyacol, and Ludox (DuPont). The selected sol should have silica particles that are discrete and of the appropriate size specified herein. The silica sol may be treated to provide a highly acidic silica sol (e.g., nitrate stabilized) that can be mixed with the zirconia sol without gelation.

The zirconia sol may be obtained using a process described, for example, in U.S. Pat. No. 6,376,590 (Kolb, et al.), or U.S. Pat. No. 7,429,422 (Davidson et al.) the disclosures of which are incorporated by reference herein. As used herein, the term "zirconia" refers to various stoichiometries for zirconium oxides, most typically $ZrO_2$, and may also be known as zirconium oxide or zirconium dioxide. The zirconia may contain up to 30 weight percent of other chemical moieties such as, for example, $Y_2O_3$ and organic material.

The silica-zirconia nanoclusters can be prepared by mixing together the nanosilica sol with the nanozirconia sol, and heating the mixture to at least 450° C. Typically, the mixture is heated for 4 to 24 hours at a temperature between about 400 to about 1000° C., more typically from about 450 to about 950° C., to remove water, organic materials, and other volatile components, as well as to potentially weakly aggregate the particles (not required). Alternatively, or in addition, the sol mixture may undergo a different processing step to remove water and volatiles. The resulting material may be milled or ground and classified to remove large aggregates. The filler may then be surface treated with, for example, a silane prior to mixing with a resin.

Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns.

In some embodiments, the composition may include acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses for certain embodiments may be preferred, since the glass typically contains sufficient elutable fluoride ions so that the thermally cured composition will have cariostatic properties. Such glass can be made from a melt containing fluoride, alumina, and other glass-forming ingredients using techniques familiar to those skilled in the FAS glassmaking art. The FAS glass, if present, is typically in the form of particles that are sufficiently finely divided so that they can conveniently be mixed with the other components and will perform well when the resulting mixture is used in the mouth.

Generally, the average particle size (typically, diameter) for FAS glass used in such compositions is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.).

Another class of useful filler are bioactive glasses and cermics. Examples include BIOGLASS (U.S. Biomaterials; Alachua, Fla.); BIO-GRAN (Orthovia; Malvern, Pa.); CERABONE A-W (Nippon Electric Glass, Japan); glasses comprising calcium oxide, silicon oxide, and phosphorous oxide; and the various phases of calcium phosphate including hydroxyapatite, monetite, brushite, and whitlockite.

Other suitable fillers are disclosed in U.S. Pat. Nos. 6,387,981 (Zhang et al.); U.S. Pat. No. 6,572,693 (Wu et al.); U.S. Pat. No. 6,730,156 (Windisch); and U.S. Pat. No. 6,899,948 (Zhang); as well as in International Publication No. WO 03/063804 (Wu et al.). Filler components described in these references include nanosized silica particles, nanosized metal oxide particles, and combinations thereof. Nanofillers are also described in U.S. Patent Publication Nos. 2005/0252413 (Kangas et al.); 2005/0252414 (Craig et al.); and 2005/0256223 (Kolb et al.).

For certain embodiments, including any one of the above embodiments, preferably the filler is selected from the group consisting of metal oxide nanoclusters, heavy metal oxide nanoparticles (zirconia nanoparticles), non-heavy metal oxide nanoparticles (e.g. silica nanoparticles), and a combination thereof.

The surface of the filler particles may be surface treated, such as with a coupling agent to enhance the bond between the filler particles and the polymerizable resin. The coupling agent may be functionalized with reactive curing groups, such as acryloyloxy, methacryloyloxy, methacrylamido, and the like. Suitable coupling agents for silane-treating filler particles include gamma-methacryloxypropyltrimethoxysilane, gamma-mercaptopropyltriethoxysilane, gamma-aminopropyltrimethoxysilane, and the like. For certain embodiments, preferably the filler is selected from the group consisting of silane-treated zirconia-silica ($ZrO_2$—$SiO_2$) fillers and nanofillers, silane-treated silica fillers and nanofillers, silane-treated zirconia fillers and nanofillers, and combinations thereof.

The thermally activated initiator is chosen such that appreciable amounts of free-radical initiating species are not produced at temperatures below about 100° C. "Appreciable amounts" refers an amount sufficient to cause polymerization and/or crosslinking to the extent that a noticible change in properties (e.g., viscosity, moldability, hardness, etc.) of the composition occurs. In addition, the temperature required for activation of the initiator to produce appreciable amounts of the free-radical initiating species does not exceed 150° C. For certain embodiments, the initiator is activated within the temperature range of 120 to 140° C., or, in some embodiments, 130 to 135° C. For certain of these embodiments, the initiator is an organic peroxide which can be thermally activated to produce appreciable amounts of free-radical initiating species within any of these temperature ranges. For certain of these embodiments, the initiator is selected from the group consisting of dicumyl peroxide, t-butyl peroxide, and a combination thereof. For certain of these embodiments, the initiator is dicumyl peroxide. In other embodiments, the initiator is selected from 2,5-Bis (tert-butylperoxy)-2,5-dimethylhexane; 2,5,-Bis(tert-Butylperoxy)-2,5-dimethyl-3-hexyne; Bis(1-(tert-butylperoxy)-1-methylethy)benzene; tert-butyl peracetate; tert-butyl peroxybenzoate; cumene hydroperoxide; 2,4-pentanedione peroxide; peracetic acid, and combinations thereof.

For certain embodiments, the thermally activated initiator is present in the composition in an amount of at least 0.2 percent based upon the weight of the polymerizable resin. For certain of these embodiments, the initiator is present in an amount of at least 0.5 percent. For certain of these embodiments, the initiator is present in the composition in the amount of not more than 3 percent based upon the weight of the polymerizable resin. For certain of these embodiments, the initiator is present in an amount of not more than 2 percent.

In certain embodiments, the composition may additionally be photopolymerizable, i.e., the composition contains a photoinitiator system that upon irradiation with actinic radiation initiates polymerization (curing or hardening) of the composition. Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Suitable iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Suitable photosensitizers are monoketones and diketones that absorb some light within a range of 400 nm to 520 nm (preferably, 450 nm to 500 nm). Particularly suitable compounds include alpha diketones that have light absorption within a range of 400 nm to 520 nm (even more preferably, 450 to 500 nm). Suitable compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other useful photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. Nos. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

The phosphine oxide initiator may be used in the photopolymerizable composition in catalytically effective amounts, such as from 0.1 weight percent to 5.0 weight percent, based on the total weight of the unfilled composition.

Tertiary amine reducing agents may be used in combination with an acylphosphine oxide. Illustrative tertiary amines useful in the invention include ethyl 4-(N,N-dimethylamino)benzoate and N,N-dimethylaminoethyl methacrylate. When present, the amine reducing agent is present in the photopolymerizable composition in an amount from 0.1 weight percent to 5.0 weight percent, based on the total weight of the unfilled composition. Useful amounts of other initiators are well known to those of skill in the art.

The composition includes a polymerizable resin having free radically active functional groups and which may include monomers, oligomers, and polymers. Suitable compounds contain at least one ethylenically unsaturated bond and can undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652, 274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO 00/38619 (Guggenberger et al.), WO 01/92271 (Weinmann et al.), WO 01/07444 (Guggenberger et al.), WO 00/42092 (Guggenberger et al.) and fluoropolymer-functional (meth) acrylates as disclosed, for example, in U.S. Pat. No. 5,076, 844 (Fock et al.) and U.S. Pat. No. 4,356,296 (Griffith et al.), EP 0373 384 (Wagenknecht et al.), EP 0201 031 (Reiners et al.), and EP 0201 778 (Reiners et al.). Mixtures of two or more free radically polymerizable compounds can be used if desired. In some embodiments, a methacryloyl-containing compound may be utilized.

The polymerizable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from commercial sources, such as Sigma-Aldrich, St. Louis. Mixtures of ethylenically unsaturated compounds can be used.

In certain embodiments, the polymerizable resin includes a compound selected from the group consisting of dimethacrylates of polyethylene glycols of 200 to 1000 weight average molecular weight, such as PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), 4 to 10 mole ethoxylated Bisphenol-A dimethacrylate (Bis-EMA), such as bisEMA6 as described in U.S. Pat. No. 6,030,606 (Holmes), NPGDMA (neopentylglycol dimethacrylate), glycerol dimethacrylate, 1,3-propanediol dimethacrylate and 2-hydroxethyl methacrylate. Various combinations of these hardenable components can be used. For certain embodiments, including any one of the above embodiments, the polymerizable resin comprises a compound selected from the group consisting of 2,2-bis[4-(2-hydroxy-3-methacryloyloxypropoxy)phenyl]propane (bisGMA), triethyleneglycol dimethacrylate (TEGDMA), urethane dimethacrylate (UDMA), 4 to 10 mole ethoxylated Bisphenol-A dimethacrylate (bisEMA), dimethacrylates of polyethylene glycols of 200 to 1000 weight average molecular weight, glycerol dimethacrylate, 1,3-propanediol dimethacrylate, and a combination thereof.

The compositions and mill blocks provided herein may optionally comprise additives suitable for use in the oral environment, including colorants, agents that impart fluorescence and/or opalescence, dyes (including photobleachable dyes), pigments, flavorants, indicators, inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

As indicated above, the present composition when thermally cured is a high strength composite suitable for use as a mill block. The composition may be conveniently cured by placing the composition in a mold and heating the composition in the range of about 100 to about 150° C. for a time sufficient for the composition to fully harden. In one example, the composition may be heated at about 130° C. for 4 hours. The temperature and the time may be varied according to the particular initiator selected, the particular composition of the polymerizable resin, and the particular filler and amount thereof utilized in the composition.

Further uses of the present composition when thermally cured include high strength molded dental articles such as crowns, bridges, denture teeth, inlays, onlays, implant abutments, veneers, implants and implant accessories, and posts. These dental articles can be molded in near-net shape (i.e. slightly oversized to allow for final shape and size adjustments) or net shapes requiring little or no further adjustment.

As used herein, an implant abutment is any component of a dental prosthetic that lies between a dental implant inserted into the jaw, and the outermost occlusal surface of a prosthetic tooth. Examples of implant abutments may be found in PCT Publication WO 2010/088754 A1, and U.S. Pat. No. 6,283,753 (Willoughby), the disclosures of both of which are incorporated by reference in their entirety.

The dental composition may be prepared using standard methods for compounding a paste. Methods which optimize mixing and minimize the presence of voids are preferred. For example, application of vacuum or pressure during compounding, forming, and/or thermally curing the composition may be used. In addition to application of heat during the curing stage, because of the above described selection of initiators, the composition may be heated (below about 100° C.) during handling and mixing without formation of appreciable amounts of free radical initiating species. This provides significant flexibility in the manufacturing process for reducing viscosity and making the composition sufficiently flowable for ease of transferring the composition and filling a mold with the composition without voids.

For certain embodiments, the present mill block or dental article may be fabricated using any one of the method embodiments described herein and incorporating the following steps: a) compounding the composition into a uniformly mixed paste, b) extruding the paste into a mold, c) curing the paste using heat or a combination of heat and light, d) removing the block or article from the mold, and if necessary, trimming excess material, and optionally e) mounting the block on a holder stub. Compounding may be carried out by dissolving the initiator in the polymerizable resin and mixing the resin with the filler.

Figure 1:
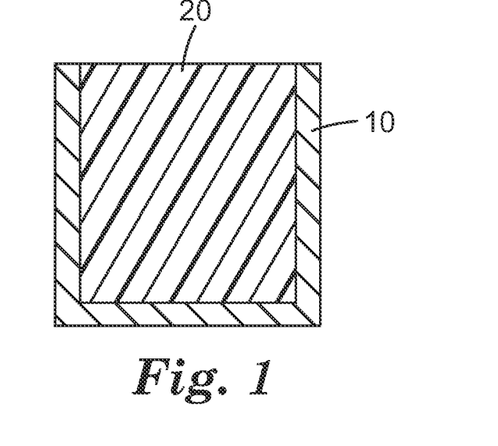
FIG. 1 is a side cross-sectional view of an exemplary embodiment of a mill block and an exemplary embodiment of a mold for making the mill block.

FIG. 1 illustrates mill block 20 contained within mold 10 after thermally curing the dental composition to form the composite material of which mill block 20 is comprised. Mill block 20 may be made in a variety of shapes and sizes, including cylinders, bars, cubes, polyhedra, ovoids, disks (pucks) and plates. Mill blocks may be made large enough, e.g. a 10 cm puck, to be used for milling multiple restorations, or even custom shapes such as a horseshoe shape for milling a full dental arch in the case of dentures. Mold 10 may be made of various materials including stainless steel, cobalt alloys, nickel alloys, aluminum alloys, plastic, glass, ceramic, or combinations thereof. Alternatively, a variety of methods of forming and shaping the blocks into any desired configuration can be employed, such as injection molding, centrifugal casting, and extrusion. During polymerization and curing, compression from springs or other means may optionally be used to reduce internal stresses.

Curing may be performed in one or multiple stage methods. In a two-stage process, initial curing may provide a material which can sustain the forces of milling or carving. The second curing stage, therefore, can be performed on the composite after a prosthetic is milled from a block.

Figure 2:
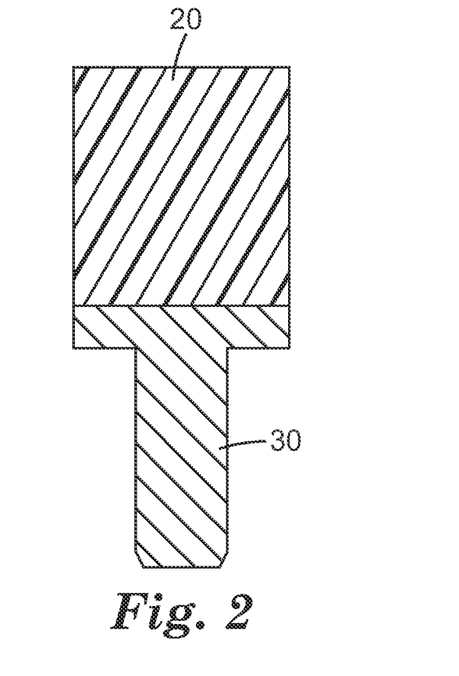
FIG. 2 is a side cross-sectional view of an exemplary embodiment of a mill block having a handle attached thereto.

Cured mill blocks, such as mill block 20 in FIG. 2, may be attached to mounting stubs, such as mandrel 30 illustrated in FIG. 2, thus facilitating affixation of the block in a milling machine as the block is milled by the machine. The mill blocks may further be provided in an frame, or simply provided without any additional support structure.

Strength of the resulting thermally cured composite may be determined in various ways, for example flexural strength and diametral strength may be measured. For certain embodiment, including any one of the above embodiments, when thermally cured the composition has a flexural strength of at least 180 MPa according to Test Method I, which is described below.

For certain embodiments, the composition when thermally cured has additional properties which are improved over previous composites used to make mill blanks. The ability to retain gloss after multiple brushings is desirable for maintaining an aesthetically pleasing appearance. Polish retention relates to the ability of the material to retain a high gloss after multiple toothbrushings. This may be determined by measuring gloss at a particular angle, for example, 60 degrees, to the surface of the cured composite initially and after various numbers of brush strokes. When the gloss after brushing is divided by the initial gloss, the gloss retention is determined. For certain embodiments, the polish retention of the composition when thermally cured is at least 90 gloss units ($G_F$) after 3000 brush strokes according to Test Method II. Other composite materials similarly tested have a polish retention of less than 80 percent, less than 60 percent, or event less than 40 percent.

In another example, the ability to withstand abrasion with a minimal amount of the material wearing away is desirable for durability of the material. This may be determined, for example, by subjecting the cured composite to a 3-body wear test wherein the reduction in thickness of the material after a number of contact cycles with an abrasive material is measured. For certain embodiments, the wear loss of the composition when thermally cured is less than 7 micrometers after 200,000 cycles according to Test Method III. Other composite materials similarly tested had a wear loss of over 8, over 9, or even over 50 micrometers. (See Examples Section, Table 7, showing thermally cured material at 3.5 micrometers loss, vs. 9.9 micrometers for the light cured material).

Various means of milling the mill blocks of the present invention may be employed to create custom-fit dental prosthetics having a desired shape and morphology. The term "milling" as used herein means abrading, polishing, controlled vaporization, electronic discharge milling (EDM), cutting by water jet or laser or any other method of cutting, removing, shaping or carving material. While milling the blank by hand using a hand-held tool or instrument is possible, preferably the prosthetic is milled by machine, including computer controlled milling equipment, However, a preferred device to create a prosthetic and achieve the full benefits of the composite material is to use a CAD/CAM device capable of milling a block, such as the Sirona Cerec 2 machine. By using a CAD/CAM milling device, the prosthetic can be fabricated efficiently and with precision.

During milling, the contact area may be dry, or it may be flushed with a lubricant. Alternatively, it may be flushed with an air or gas stream. Suitable lubricants are well known in the art, including water, oil, glycerin, ethylene glycols, and silicones. After machine milling, some degree of finishing, polishing and adjustment may be necessary to obtain a custom fit into the mouth and/or aesthetic appearance.

A milled dental prosthetic an be attached to a tooth or bone structure with conventional cements or adhesives or other appropriate means such as glass ionomer, resin cement, zinc phosphate, zinc polycarboxylate, or resin-modified glass. In addition, material may optionally be added to a milled prosthetic for various purposes including repair, correction, or enhancing esthetics. The additional material may be of one or more different shades or colors. The added material may be composite, ceramic, or metal.

As indicated above, a kit comprising a plurality of mill blocks is provided. The mill blocks can be any of those described herein and prepared according to the thermal curing methods described herein. The mill blanks may be of various sizes, with some large enough to create multiple restorations. In some kits, mill blanks of various colors may be provided to better match a patient's teeth.

Objects and advantages of this invention are further illustrated by the following examples, but the particular materials and amounts thereof recited in these examples, as well as other conditions and details, should not be construed to unduly limit this invention.

EXAMPLES

The trade designations of products referred to in the following Examples and throughout the present specification are stated in all capitol letters.

Unless otherwise noted, reagents and solvents were obtained from Sigma-Aldrich Corp., St. Louis, Mo.

As used herein:

"bisGMA" refers to 2,2-bis[4-(2-hydroxy-3-methacryloyloxypropoxy)phenyl]propane;

"TEGDMA" refers to triethyleneglycol dimethacrylate, obtained from Sartomer Co., Inc., Exton, Pa.;

"UDMA" refers to diurethane dimethacrylate, obtained under the trade designation "ROHAMERE 6661-0" from Rohm America LLC, Piscataway, N.J.;

"BisEMA-6" refers to ethoxylated bisphenol A dimethacrylate, obtained from Sartomer Co., Inc., Exton, Pa.;

"BHT" refers to butylated hydroxytoluene;

"BZT" refers to 2-(2-hydroxy-5-methacryloxyethylphenyl)-2H-benzotriazole obtained from Ciba, Inc., Tarrytown, N.Y.;

"CPQ" refers to camphorquinone;

"DFIHFP" refers to diphenyliodonium hexafluorophosphate, obtained from Johnson Matthey, Alpha Aesar Division, Ward Hill, N.J.;

"ENMAP" refers to ethyl-(N-methyl-N-phenyl)amino propionate, synthesized using known methods, such as those described by Adamson, et al.; JCSOA9; J. Chem. Soc.; 1949; spl. 144, 152, which is incorporated herein by reference;

"IRGACURE 819" refers to a Bis(2,4,6-Trimethylbenzoyl)phenylphosphine oxide obtained from Ciba, Inc., Tarrytown, N.Y.;

"PEG 600 DM" refers to Polyethylene Glycol Dimethacrylate, avg MW ~600, available from Sartomer Co., Inc., Exton, Pa.;

"ST Nanozirconia" refers to silane treated zirconia nanoparticles prepared as described in US 2005/0256223.

"ST 20 nm Silica" refers to silane treated silica particles having an average particle diameter of 20 nanometers prepared as described in U.S. Pat. No. 6,899,948; and "ST Silica/Ziconia Clusters" refers to silane treated silica-zirconia nanocluster filler prepared as described in U.S. Pat. No. 6,730,156.

Paste Preparation

Example 1

Thermally Curable Paste

To a polymerizable resin (100.05 g) made up of ethylenically unsaturated compounds in the amounts shown in Table 1 was added 1.27 g of dicumyl peroxide with stirring at room temperature until dissolved.

TABLE 1

Polymerizable Resin Composition

| Compound | Amount (wt %) |
|---|---|
| 90/10 BisGMA/TEGDMA | 12.027 |
| BisGMA | 14.189 |
| UDMA | 35 |
| BisEMA-6 | 35 |
| PEG 600 DM | 3.784 |

A paste was prepared by combining the above resin and fillers as shown in Table 2 and mixing until a uniform paste was formed.

TABLE 2

Paste Composition

| Component | Amount (g) |
|---|---|
| Polymerizable resin | 4.4018 |
| ST Nanozirconia | 0.8194 |
| ST 20 nm Silica | 1.5231 |
| ST Silica/Ziconia Clusters | 13.26 |

Example 2

Light Curable Paste (Comparative)

A paste was prepared as in Example 1, except that a photoinitiator package made up of the components and amounts (wt % of the resin) shown in Table 3 was substituted for the dicumyl peroxide:

TABLE 3

Photoinitiator Package

| CPQ | 0.22 |
|---|---|
| DFIHFP | 0.35 |
| Igracure 819 | 0.05 |
| ENMAP | 0.81 |
| BHT | 0.15 |
| BZT | 0.125 |

Test Method I—Flexural Strength

Sample preparation, thermal cure: An Example 1 paste sample was pressed at 65 deg. C. in a preheated glass mold to form a 2 mm×2 mm×25 mm test bar. The bar was thermally cured in an oven for 4 hours at 140 deg. C. under oxygen exclusion and sanded lightly with 600-grit sandpaper to remove flash from the molding process.

Sample preparation, comparative light cure: An Example 2 comparative paste sample was pressed at 65 deg. C. in a preheated mold to form a 2 mm×2 mm×25 mm test bar. The bar was aged at room temperature for 24 hours and light cured for 90 seconds by exposure to two oppositely disposed VISILUX Model 2500 blue light guns (3M ESPE). The bar was then post-cured for 180 seconds in a Dentacolor XS unit (Kulzer, Inc., Germany) light box, and sanded lightly with 600-grit sandpaper to remove flash from the molding process.

After storing the samples in distilled water at 37 deg. C. for 24 hours, the Flexural Strength of the bars was measured on an Instron tester (Instron 4505, Instron Corp., Canton, Mass.) according to ANSI/ADA (American National Standard/American Dental Association) specification No. 27 (1993) at a crosshead speed of 0.75 mm/minute. Multiple replicates were analyzed and the results were reported in megapascals (MPa).

Flexural strength results are shown in Table 4

TABLE 4

Flexural Strength

| Example | Flexural Strength (MPa) | Std. Deviation (MPa) |
|---|---|---|
| Thermally cured | 194.5 | 15.1 |
| Light cured (run 1) | 155 | 15 |
| Light cured (run 2) | 119.7 | 11.3 |

Test Method II—Polish Retention

Sample preparation, thermal cure: Rectangular-shaped samples of the Example 1 paste were pressed into a 20 mm long×9 mm wide×3 mm thick airtight mold and cured in an oven at 130 deg. C. for 4 hours under oxygen exclusion.

Sample preparation, comparative light cure: Rectangular-shaped samples of the Example 2 comparative paste were pressed into a 20 mm long×9 mm wide×3 mm thick mold and cured with a XL3000 curing light (3M ESPE) for 30 seconds per side in 4 locations covering the sample.

The cured samples were mounted with double-sided adhesive tape (Scotch Brand Tape, Core series 2-1300, St. Paul, Minn.) to a holder and were polished according to the following series of steps that were performed sequentially as shown in Table 1. A Buehler ECOMET 4 Polisher with an AUTOMET 2 Polishing Head (Buehler Ltd., Lake Bluff, Ill.) was used with clockwise rotation.

TABLE 5

Polishing steps

| Step | Procedure | Abrasive Grit | Lubricant | RPM | Load (lb) per sample | Time (seconds) |
|---|---|---|---|---|---|---|
| 1 | Polish | SiC-320 | Water | 150 | 1 | 15 |
| 2 | Rinse | | Water | | | |
| 3 | Polish | SiC-600 | Water | 150 | 1 | 60 |
| 4 | Rinse | | Water | | | |
| 5 | Polish | Cloth-9 um slurry | Water | 130 | 1 | 120 |
| 6 | Rinse | | Water | | | |
| 7 | Polish | Cloth-3 um slurry | Water | 130 | 1 | 120 |
| 8 | Rinse | | Water | | | |
| 9 | Master Polish | Master Polish Abrasive | Water | 120 | 0.75 | 100 |
| 10 | Rinse | | Water | | | |

After polishing, the samples were then placed in deionized water in an oven at 37.degree. C. for 24 hours prior to testing.

A micro-tri-gloss instrument (BYK Gardner, Columbia, Md.) was used to collect photoelectric measurements of specularly reflected light from the sample surface after polishing and after toothbrushing. The procedure described in ASTM D 523-89 (Reapproved 1994) Standard Test Method for Specular Gloss, for measurements made at 60 degree geometry was followed with the following modification. Initial gloss after polishing ($G_I$) was measured for initial sample. Gloss was measured after various numbers of toothbrushing cycles ($G_F$). Randomly selected areas on the rectangular sample were measured for initial and brushed gloss. Each sample was brushed for up to 6000 cycles with an ORAL B 40 medium Straight toothbrush (Oral B Laboratories, Belmont, Calif.) using CREST Regular Flavor (Proctor & Gamble, Cincinnati, Ohio) toothpaste. One operator brushed all of the samples using forces on the order of toothbrushing forces. Each sample was brushed with the same toothbrush. One toothbrushing cycle was a forward and a back stroke. Percent polish retention was reported as ($G_F \times 100)/G_I$ or just as the final gloss for a given set of toothbrush strokes ($G_F$) and was the average of several replicates.

Polish retention results are shown in Table 6.

TABLE 6

Polish Retention

| Example | 60 Degree gloss | % Gloss Retention | Number of Brush Strokes |
| --- | --- | --- | --- |
| Thermally cured | 95 | | Initial, no brushing |
| Light cured | 92 | | Initial, no brushing |
| Thermally cured | 89 | 94 | 3,000 |
| Light cured | 75 | 82 | 3,000 |
| Thermally cured | 87 | 92 | 6,000 |
| Light cured | 77 | 84 | 6,000 |

Test Method III—3-Body Wear

The wear rate of cured test samples was determined by an in-vitro 3-body wear test using a Davidson Wear Tester Model 2 (ACTA, Amsterdam) unit. The Davidson Wear Tester was calibrated to ensure that the wear track was perpendicular to the wheel face. Sample slots on the wear wheel were alternately filled with Example 2 comparative, light cured samples and Example 1 thermally cured samples such that every other slot had the thermally cured samples. The technique of alternating sample and comparative slots compensates for machine-to-machine variability that may be found in this type of test.

Example 1 paste samples were pressed into a preheated airtight mold at 65 deg. C. to form bars of an appropriate size to fit into the slots of the wear wheel (approximately 4 mm×4 mm×10 mm). The bars were thermally cured in an oven at 130 deg. C. for 4 hours under oxygen exclusion. After being trimmed to the proper length by a diamond saw, the bars were loaded into 10-mm by 4-mm slots on a 47.75 mm diameter wear wheel of the Davidson Wear Tester.

Example 2 comparative paste materials were placed into the adjacent slots and cured for 20 seconds per layer using an XL3000 Curing Light (3M Company). 3 layers were needed to fill each slot to insure complete cure through the thickness of the paste. The samples on the wheel were then put into an Visio Beta Vario light box (3M ESPE) and light cured for 14 additional minutes under vacuum. The wheel including the attached samples was placed into 37 deg. C. deionized water for 24 hours prior to testing.

The wear wheel, with the cured samples mounted (constituting the first body), measured 50.80 to 53.34 mm in diameter. The cured samples on the wear wheel were machined smooth using a Carter Diamond Tool device (S-2192 SYN, Carter Diamond Tool Corp., Willoughby, Ohio) turning at 900 rpm. Water was flooded onto the wheel to control dust and to dissipate heat during the machining process. The wear wheel was kept as wet as possible during the machining The final diameter of the first body wear wheel was 48.26 mm.+−.0.254 to 0.381 mm.

During testing, the first body was allowed to contact another wheel (constituting the second body) that acted as an antagonistic cusp. During contact, the two wheels were immersed in a slurry (constituting the third body) having 120 grams of low-fat white rice ground for 60 seconds in a coffee grinder, 30 grams millet husks ground with the above white rice for 60 seconds in a waring blender, and 275 ml of ACTA buffer solution (1000 g of DI water to 41.1 g of KH2PO4 and 9.3 g NaOH). The two wheels were counter-rotated against each other in 40,000 cycle increments up to 200,000 cycles. Dimensional loss during these cycles was measured every 40,000 cycles by a Perthometer PRK profilometer (Feinpruef Corp., Charlotte, N.C.) along the 10-mm face of the cured and machined composite. Data were collected in a Wear Version 3 software (ACTA, Amsterdam). The data were plotted using linear regression and the wear rates for the samples were determined by calculating the slope of the lines. The wear rate for each sample was reported as a change in unit length per number of cycles (e.g., mm/cycle) and can be reported as a micron depth of wear.

3-body wear results are shown in Table 7. Microns of wear (loss of material) is shown 200,000 wear cycles.

TABLE 7

3-Body Wear

| Example | Micrometers lost |
| --- | --- |
| Thermally cured | 3.5 |
| Light cured | 9.9 |

Diametral Tensile Strength (DTS)

Sample preparation, thermal cure: An Example 1 paste sample was injected into a 4 mm (inside diameter) glass tube, the tube was capped with silicone rubber plugs, and then the tube was compressed axially at approximately 2.88 kg/cm$^2$ pressure for 5 minutes. The tube was placed in an oven at 130 deg. C for 4 hours to cure the paste.

Sample preparation, comparative light cure: An Example 2 paste sample was injected into a 4-mm (inside diameter) glass tube; the tube was capped with silicone rubber plugs; and then the tube was compressed axially at approximately 2.88 kg/cm$^2$ pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany).

Cured samples were then were cut with a diamond saw to form 2 mm long cylindrical plugs for measurement of compressive strength. The plugs were stored in deionized water at 37 deg. C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27).

Diametral tensile strength results are shown in Table 8.

TABLE 8

| Diametral Tensile Strength (DTS) | | |
|---|---|---|
| Example | DTS (MPa) | Std. Deviation(MPa) |
| Thermally cured | 100.8 | 12.6 |
| Light cured | 83.1 | 4.2 |

Mill Blank and Crown Formation

The paste of Example 1 was cured into an approximately 20 mm×22 mm×20 mm cube form in a silicone mold having a cavity and sandwiched between two metal plates. Between the metal plates and paste was polyester film to exclude oxygen and provide a smooth surface finish to the mill blank. The assembled and clamped mold was placed into an oven at 130 deg. C. for 4 hours. The cured blank was removed from the mold and attached to a Lava Frame (3M ESPE) using Scotch-Weld CA8 adhesive (3M).

A crown was designed by scanning a typical model of dentition, particularly the preparation adjacent and opposing tooth data and creating a digital file using the Lava Scan ST (3M ESPE). The digital file was used to design the crown using Lava Design Software (3M ESPE), the crown being a typical molar. A Lava Milling System (3M ESPE) was used to mill the crown. After milling, the finial polishing was done using standard composite polishing kits and a handpiece. A crown having an excellent aesthetic appearance was achieved.

Prophetic Example

Formation of an Implant Abutment

The paste of Example 1 is cured into an approximately 20 mm×22 mm×20 mm cube form in a silicone mold having a cavity and sandwiched between two metal plates. Between the metal plates and paste is polyester film to exclude oxygen and provide a smooth surface finish to the mill blank. The assembled and clamped mold is placed into an oven at 130 deg. C. for 4 hours. The cured blank is removed from the mold and attached to a Lava Frame (3M ESPE) using Scotch-Weld CA8 adhesive (3M).

A screw-retained abutment for an implant is designed using a CAD/CAM system, the abutment having a shape typical for a molar and having a hex-shaped base designed to mate with a typical implant having a hex-shaped socket. A channel for a screw is designed to extend through the abutment. A mill blank is inserted into the milling module of the CAD/CAM system and the abutment design is milled, thus forming an implant abutment.

The implant abutment is placed into the implant, a screw is inserted into the channel and tightened, the screw channel is optionally filled with a curable dental composite, and a previously prepared crown is cemented onto the abutment, thus forming an implant-based restoration.

Example

Formation of a Net Shape Dental Crown by Molding

A mold was made by packing Imprint 3 VPS Impression Material (3M ESPE) into a small speed mixer cup. A molar-shaped typodont was pressed into the impression material and the material was allowed to cure at room temperature for about 10 minutes. The cured mold was sliced in half, allowing the typodont to be removed. The two halves of the mold were reinserted into the supporting cup, thus forming a mold for a molar shape.

The paste described in Example 1, further including a small percentage (approximately 0.05% by wt.) of pigment for shading, was heated to 85 deg. C. and pressed into the mold, overfilling the mold such that the cap to the speed-mixer cup could be screwed on, applying slight pressure to the filled mold. The assembled mold and paste were placed into a nitrogen-purged oven and held at 125 deg. C. for 8 hours. The thermally cured dental crown was removed from the mold. The crown had good replication detail of the original typodont and had a glossy surface finish, requiring no further polishing.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

The complete disclosures of the patents, patent documents, and publications cited herein are incorporated by reference in their entirety or the portions of each that are indicated as if each were individually incorporated.

What is claimed is:

1. A method of manufacturing a dental mill block, the method comprising:
   providing a composition comprising:
      a polymerizable resin comprising an ethylenically unsaturated group;
      a thermally activatable initiator dissolved in the resin; and
      an inorganic filler combined with the resin, wherein the filler is present in an amount of at least 60 percent by weight based upon the weight of the composition;
      wherein the initiator is activatable at a temperature of about 100 to about 150° C. to provide free radicals; and
      wherein the inorganic filler comprises nanoclusters comprising silica nanoparticles and at least one other metal oxide, wherein the silica nanoparticles are prepared from a silica sol comprising silica nanoparticles;
   wherein the nanoclusters have a surface area of at least 65 square meters per gram;
   shaping the composition into a desired mill block configuration; and
   thermally curing the composition at a temperature of about 100° C. to about 150° C.

2. The method of claim 1, the wherein the surface area of the nanoclusters is at least 80 square meters per gram filler.

3. The method of claim 1, wherein the filler is present in an amount of at least 75 percent by weight based upon the weight of the composition.

4. The method of claim 1, wherein the at least one other metal oxide comprises heavy metal oxide, non-heavy metal oxide, or a combination thereof.

5. The method of claim 1, wherein the initiator is selected from the group consisting of dicumyl peroxide, t-butyl peroxide, 2,5-bis(tert-butylperoxy)-2,5-dimethylhexane; 2,5-bis(tert-butylperoxy)-2,5-dimethyl-3-hexyne; bis(1-

(tert-butylperoxy)-1-methylethyl)benzene; tert-butyl peracetate; tert-butyl peroxybenzoate; cumene hydroperoxide; 2,4-pentanedione peroxide; peracetic acid, and combinations thereof.

6. The method of claim 5, the wherein the initiator is dicumyl peroxide.

7. The method of claim 1, wherein the initiator is present in the composition in an amount of about 0.2 to about 3 percent based upon the weight of the polymerizable resin.

8. The method of claim 1, wherein the polymerizable resin comprises a compound selected from the group consisting of 2,2-bis[4-(2-hydroxy-3-methacryloyloxypropoxy)phenyl] propane (Bis-GMA), triethyleneglycol dimethacrylate (TEGDMA), urethane dimethacrylate (UDMA), 4 to 10 mole ethoxylated Bisphenol-A dimethacrylate (Bis-EMA), dimethacrylates of polyethylene glycols of 200 to 1000 weight average molecular weight, glycerol dimethacrylate, 1,3-propanediol dimethacrylate, and a combination thereof.

9. The method of claim 1, wherein the polish retention of the composition after the step of thermally curing the composition at a temperature of about 100° C. to about 150° C. is at least 90 gloss units ($G_F$) after 3000 brush strokes according to Test Method II.

10. The method of claim 1, wherein the wear loss of the composition after the step of thermally curing the composition at a temperature of about 100° C. to about 150° C. is less than 7 microns after 200,000 cycles according to Test Method III.

11. A kit comprising a plurality of mill blocks made according to the method of claim 1.

12. The method of claim 1, wherein the nanoclusters comprise silica nanoparticles and zirconia nanoparticles.

13. The method of claim 1, wherein the silica nanoparticles comprise non-pyrogenic silica nanoparticles.

14. The method of claim 1, wherein the initiator does not produce appreciable amounts of free-radical initiating species below a temperature of 100° C.

15. A mill block prepared according to the method of claim 1.

16. An implant abutment formed from the mill block of claim 15.

17. The method of claim 1, wherein after the step of thermally curing the composition at a temperature of about 100° C. to about 150° C., the composition has a flexural strength of at least 180 MPa according to Test Method I.

* * * * *

UNITED STATES PATENT AND TRADEMARK OFFICE
CERTIFICATE OF CORRECTION

Page 1 of 2

PATENT NO. : 9,962,245 B2
APPLICATION NO. : 13/516981
DATED : May 8, 2018
INVENTOR(S) : Bradley Craig et al.

It is certified that error appears in the above-identified patent and that said Letters Patent is hereby corrected as shown below:

On the Title Page

Column 1, (Notice)
Line 3, After "0" delete "days.".

In the Specification

Column 2
Line 41, Delete ""nano structured"" and insert -- "nanostructured" --, therefor.

Column 4
Lines 3-4, Delete "micrometer" and insert -- micrometer. --, therefor.

Column 5
Line 11, Delete "Stark," and insert -- Starck, --, therefor.

Column 6
Line 18, Delete "cermics." and insert -- ceramics. --, therefor.
Line 58, Delete "noticible" and insert -- noticeable --, therefor.

Column 7
Line 9, Delete "methylethy)" and insert -- methylethyl) --, therefor.

Column 8
Line 42, Delete "hexacrylate," and insert -- hexaacrylate, --, therefor.

Column 9
Lines 29-30, Delete "2-hydroxethyl" and insert -- 2-hydroxyethyl --, therefor.

Signed and Sealed this
Fifteenth Day of January, 2019

Andrei Iancu
*Director of the United States Patent and Trademark Office*

Column 11
Line 62, Delete "equipment," and insert -- equipment. --, therefor.

Column 12
Line 8, Delete "an be" and insert -- can be --, therefor.
Line 34, Delete "capitol" and insert -- capital --, therefor.
Lines 52-53, Delete "DFIHFP" and insert -- DPIHFP --, therefor.
Line 53, Delete "Alpha" and insert -- Alfa --, therefor.
Line 54, Delete "Ward Hill, NJ" and insert -- Haverhill, MA --, therefor.

Column 13
Line 4, Delete "Silica/Ziconia" and insert -- Silica/Zirconia --, therefor.
Line 39 (Approx.), Delete "Silica/Ziconia" and insert -- Silica/Zirconia --, therefor.
Line 56 (Approx.), Delete "Igracure" and insert -- Irgacure --, therefor.
Line 56, Table 3, Delete "DFIHFP" and insert -- DPIHFP --, therefor.

Column 16
Line 11, After "machining" insert -- . --.

In the Claims

Column 18
Line 56, In Claim 2, Delete "the wherein" and insert -- wherein --, therefor.